United States Patent [19]

Barone

[11] Patent Number: 4,472,137

[45] Date of Patent: Sep. 18, 1984

[54] INSTRUMENT FOR ATTACHING ORTHODONTIC ELASTIC BANDS

[75] Inventor: Joseph I. Barone, Escondido, Calif.

[73] Assignee: Richard Guy, Laguna Niguel, Calif.

[21] Appl. No.: 465,600

[22] Filed: Mar. 10, 1983

[51] Int. Cl.³ .............................................. A61C 7/00
[52] U.S. Cl. ..................................................... 433/3
[58] Field of Search .............................. 433/3, 11, 18

[56] References Cited

U.S. PATENT DOCUMENTS 4,040,187  8/1977  Cardena ................................. 433/3
4,277,236  7/1981  Kurz ..................................... 433/3

Primary Examiner—Robert Peshock

Attorney, Agent, or Firm—Francis X. LoJacono

[57] ABSTRACT

An orthodontic instrument is provided for attaching elastic retainer rings or bands to the brackets attached to a patient's teeth, so as to secure the arch-wire member to the brackets to form the braces. The instrument includes an elongated elastic loading core having a slidable ejector housing mounted for reciprocal movement thereon. The elastic loading core includes a rear guide-stem portion, an intermediate band-support portion, and an ejector-head member. Each band is selectively positioned on the ejector head of the loading core, so as to be forced over the cleat member of the bracket by forward movement of the ejector housing, which is provided with a dispenser head.

5 Claims, 10 Drawing Figures

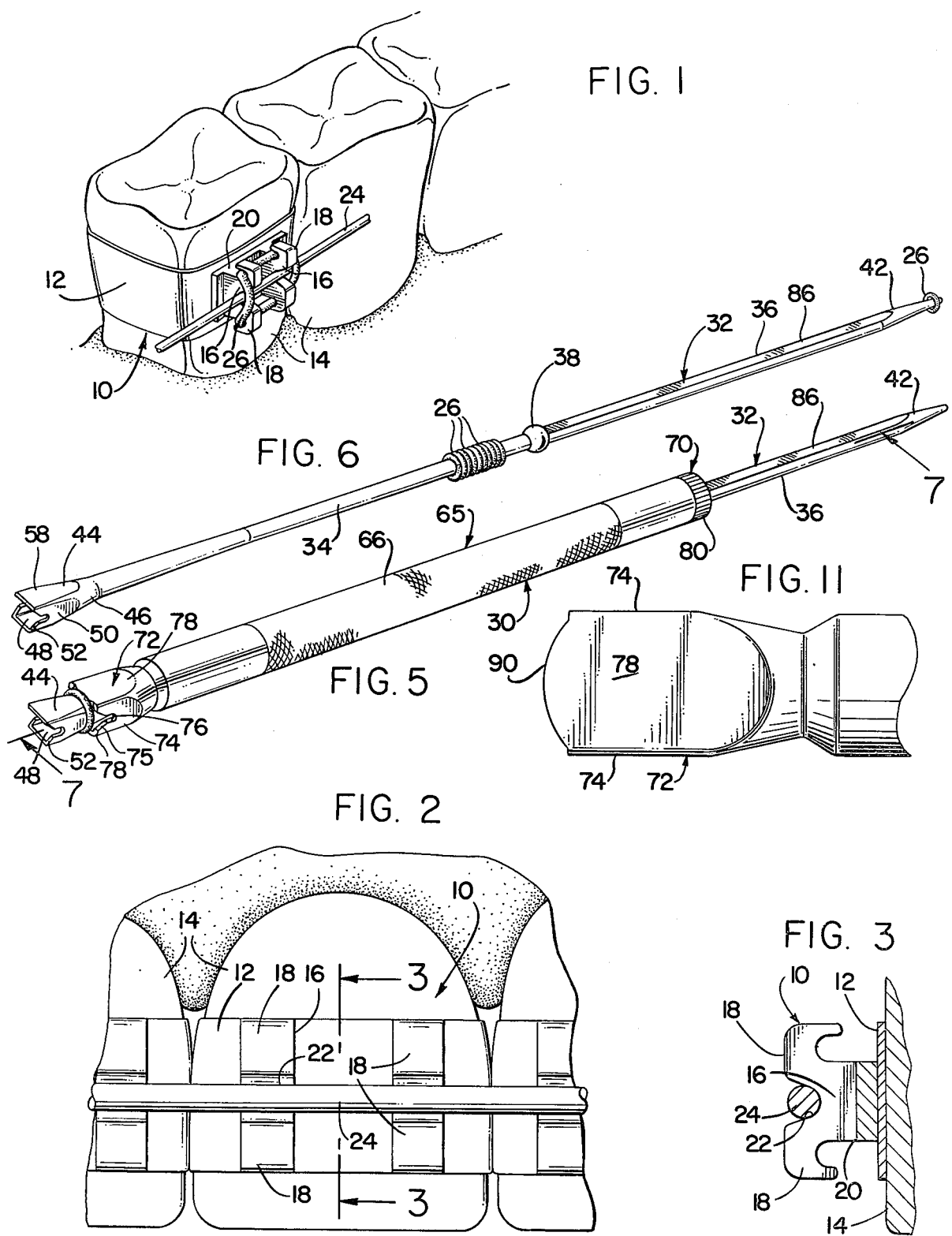

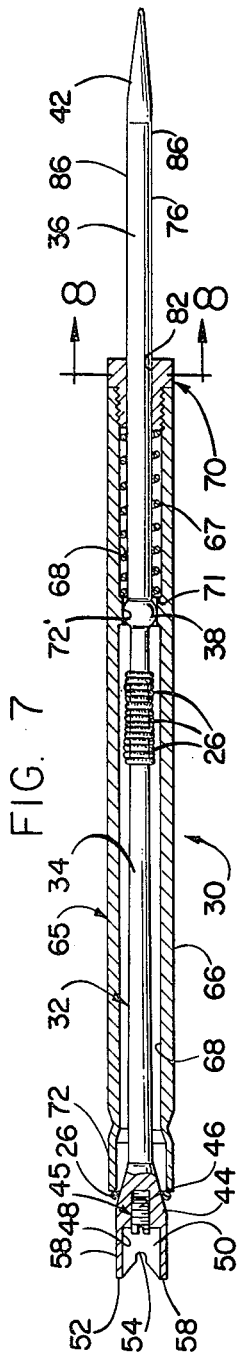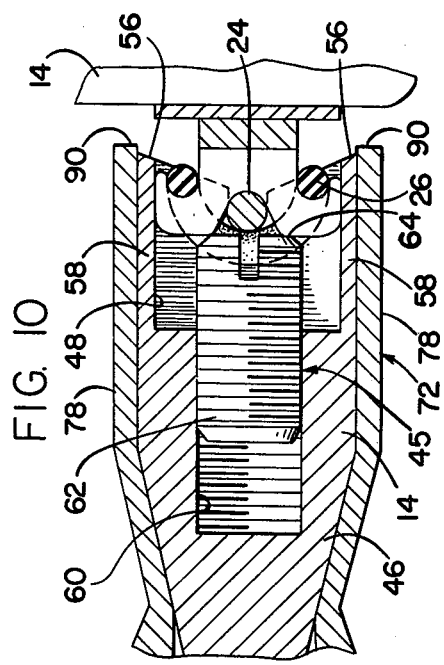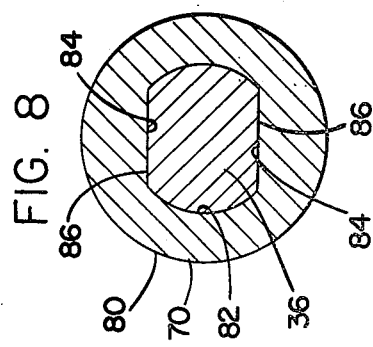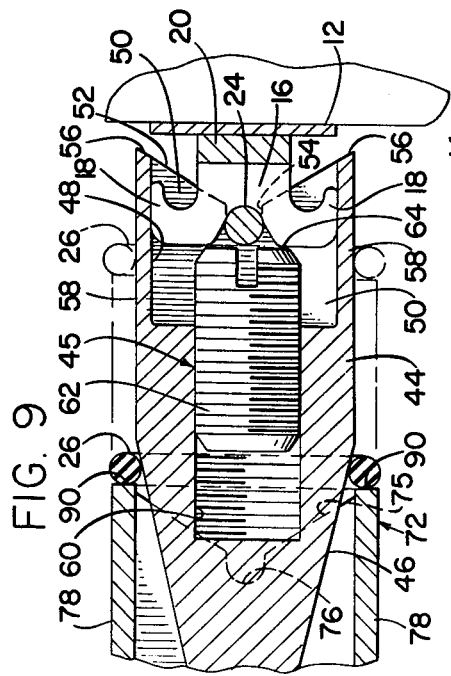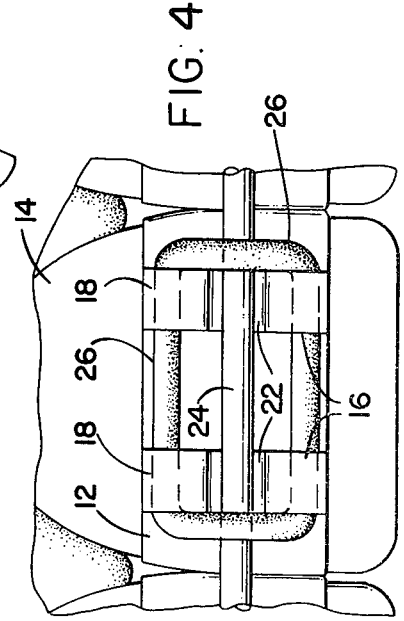

INSTRUMENT FOR ATTACHING ORTHODONTIC ELASTIC BANDS

BACKGROUND OF THE INVENTION

1. Field of the Invention

This invention relates generally to an orthodontic instrument, and more particularly to an orthodontic instrument for dispensing elastic wire-retaining bands, which are used in attaching arch wire to the wire-support brackets attached to a patient's teeth, for adjusting and repositioning the teeth.

2. Description of the Prior Art

As is well known in the art, various problems and difficulties are being encountered in attempting to provide a suitable means for applying orthodontic elastic bands to arch-wire brackets that are secured to a patient's teeth during the orthodontics process.

In most cases in the past, orthodontists have found that the conventional method of attaching the small-diameter elastic retainer bands to arch wire brackets is very unsatisfactory. Heretofore, forceps or hemostats have been used to grip the elastic bands and apply tension as they are being hooked and stretched around the opposite projecting cleats that form part of the arch-wire brackets. This well-established procedure is extremely tedious and time-consuming for the orthodontist, and is an uncomfortable experience for the patient. Also, it can be hazardous, since it is not uncommon for forceps or a hemostat to accidentally slip and release the elastic band within the patient's mouth, at times resulting in the patient swallowing the loose band. Furthermore, a bracket can be knocked loose from the tooth.

In order to overcome the above-mentioned problems, various instruments have been tried with varying success. As examples of some known devices the following United States patents are mentioned.

U.S. Pat. No. 3,360,861 to Hoffman discloses a dental band pusher and adapter instrument which includes a handle having an extended shank. The outer free end of the shank is provided with a pusher member and an oppositely disposed adapted member for manipulating the band on the teeth.

Another Hoffman patent, U.S. Pat. No. 3,458,031, relates to an orthodontic spring-clip-fastening system whereby elastic bands are eliminated as a retaining means.

U.S. Pat. No. 4,127,940 to Skilliday discloses an orthodontic instrument for applying elastic arch wire-retaining rings. This device comprises an elongated handle terminating at one end thereof in an omegoid tip portion arranged to releasably hold the elastic band or annulus while it is being stretched and applied to the opposite ends of the supporting bracket, so as to retain the arch wire therein.

U.S. Pat. No. 4,206,374 to Kurz is also designed as an elastic-band applicator which includes a U-shaped tubular housing, so that when the housing is inserted into the mouth of the patient the end of the housing may be placed against the lingual surface of a patient's tooth.

Another patent to Kurz, U.S. Pat. No. 4,277,236, discloses an orthodontic instrument for applying elastic ligatures that includes a disposable cartridge which services as a dispenser member, a housing for receiving the cartridge, a spring-biased pusher member slidably mounted in the housing to engage the rear elastic of the stack to push the stack toward the forward end of the cartridge, so that the forward elastic moves along an enlarged end portion of the cartridge, a plurality of push rods extending along the cartridge under the ligatures with the ends of the push rods engaging the forward ligature, and including a release means for moving the cartridge reciprocally with respect to the housing, so as to force an elastic over the enlarged end of the cartridge.

SUMMARY OF THE INVENTION

The present invention has for an important object to provide an orthodontic instrument for simply and easily attaching elastic bands to arch brackets, otherwise known as braces for correcting irregularities of the teeth, without any discomfort to the patient. This is accomplished with the present invention by providing an instrument that requires only a firm forward pressure or force applied to the reciprocal ejector housing, at which time an elastic band is ejected and secured to the cleats of a typical orthodontic bracket.

Another object of the invention is to provide an orthodontic instrument that includes an elongated elastic band-loading core which is arranged to receive and store a plurality of elastic bands. The core, together with the bands, are enclosed in an ejector housing or sleeve which is slidably mounted over the core, so as to be reciprocally moved with respect to the core. The dispenser head of the housing engages an elastic band, thereby forcing the band over the ejector head onto a selected bracket on which the arch wire is simultaneously secured.

Still another object of the present invention is to provide an orthodontic instrument of this character that allows the application of individual elastic bands to be performed by the orthodontist or the assistant with the use of only one hand.

A still further object of the invention is to provide an instrument of this type that is formed having an ejector-head member on the end of the loading-core member, wherein the ejector head is recessed and notched so as to accommodate the extended cleats of the arch bracket as well as the arch wire positioned thereon. This arrangement allows the elastic band to be readily stretched as it is forced over the ejector head by the dispenser head, whereby the band is ejected over the extended cleats and around the arch wire, thus securing the wire to the bracket in one simple operation.

It is a further object of the invention to provide an orthodontic instrument of this character that has relatively few operating parts.

It is still another object of the invention to provide a tool of this character that is easy to service and maintain.

Still another object of the invention is to provide an orthodontic elastic-band applicator that is relatively inexpensive to manufacture, yet is simple and rugged in construction.

The characteristics and advantages of the invention are further sufficiently referred to in connection with the accompanying drawings, which represent one embodiment. After considering this example, skilled persons will understand that variations may be made without departing from the principles disclosed; and I contemplate the employment of any structures, arrangements or modes of operation that are properly within the scope of the appended claims.

BRIEF DESCRIPTION OF THE DRAWINGS

Referring more particularly to the accompanying drawings, which are for illustrative purposes only:

FIG. 1 is a pictorial view of a typical orthodontic bracket secured to a tooth on which is mounted an arch wire that is coupled to the cleat member of the bracket by an elastic orthodontic band or ring;

FIG. 2 is an enlarged elevational view of a group of teeth having brackets mounted thereto, and ready to receive the arch wires thereon, before the elastic bands are coupled to the brackets;

FIG. 3 is a cross-sectional view of the orthodontic arch bracket taken substantially along line 3—3 of FIG. 2;

FIG. 4 is an elevational view, similar to that shown in FIG. 2, with the elastic band coupled to the bracket, thereby securing the arch wire to the bracket in the preferred and correct manner;

FIG. 5 is a perspective view of the present invention showing an elastic band positioned adjacent the ejector head prior to being ejected therefrom, and the ejector housing in a forward ejecting mode;

FIG. 6 is a perspective view of the ejector core loaded with a plurality of elastic bands;

FIG. 7 is a longitudinal cross section of the instrument taken substantially along line 7—7 of FIG. 5;

FIG. 8 is an enlarged cross-sectional view of the guide-bushing member taken along line 8—8 of FIG. 7;

FIG. 9 is an enlarged cross-sectional view of the ejector head with an elastic band being engaged by the dispenser head, and the cleats of the arch bracket being received in the cavity of the ejector head;

FIG. 10 is an enlarged cross-sectional view, similar to that of FIG. 9, with the dispenser head moved to its extreme forward position, thus causing the elastic band to snap over the inserted cleats of the bracket; and FIG. 11 is an enlarged top-plan view of the dispenser head of the ejector sleeve.

DESCRIPTION OF THE PREFERRED EMBODIMENT

Referring more particularly to FIGS. 1 through 4, there is illustrated therein one of many suitable types of orthodontic arch brackets, designated at 10. These brackets come in more than one form, the one shown having a fastening strap 12 which clamps to a tooth 14 and is formed with a pair of relatively spaced-apart and forwardly projecting cleat members 16 which terminate in opposite hook-shaped ends or ears 18 disposed in an outwardly spaced relation to the base member 20. Another form of bracket (not shown) has a base member 20 which would be affixed directly to the surface of the tooth. Each cleat 16 is formed with a centrally positioned notch or recess 22 adapted to receive the arch wire 24, which permits the wire to extend laterally to both sides thereof for additional engagement with other contiguously aligned brackets.

As is well known in the art, an elastic band or ring such as at 26 is generally formed from rubber or an elastomeric synthetic resin material having an approximate outer diameter of 3 mm. Bands 26 are stretched over lateral wire 24 and are hooked to ears 18, as seen in FIGS. 1 and 4.

Referring more particularly to the present invention, there is shown in FIG. 5 an orthodontic instrument, generally indicated at 30, comprising an elongated, longitudinal, elastic loading-core member 32 formed having an ejector head 44, an intermediate stem portion 34, and a rear guide-stem portion 36, the two portions being divided by a first spring-retainer means 38 that defines a shoulder stop for spring 67. The opposite free end of guide stem 36 is tapered at 42, allowing elastic bands 26 to be positioned on the loading core for storage and to be available for application.

Bands 26 are preferably located along intermediate stem 34, as seen in FIGS. 6 and 7. The bands are forced over shoulder stop 38, and positioned between shoulder 38 and ejector head 44, which defines the band-ejector end of core 32. Ejector head 44 is formed in a somewhat box-like configuration having four substantially flat sides and a conical trailing member 46 which allow the bands to be individually stretched over the four sides of the ejector head.

The sides of ejector head 44 define a cavity 48 so as to be adapted to receive cleats 16 therein, as illustrated in FIGS. 9 and 10. A pair of oppositely disposed side walls 50 of ejector head 44 are formed having corresponding notches 52 which are preferably tapered inwardly in a substantially V-shaped configuration, each notch including a countersunk recess 54. The countersunk recess 54 allows arch wire 24 to engage therein, thereby defining a positioning means for the wire as the instrument is placed over the bracket cleats, and further allows the tapered sides of the V-shaped notches to be positioned just beyond the hooked ear members 18, as seen in FIGS. 9 and 10.

However, since there are several types and forms of arch brackets having various sizes of cleats, the ejector head 44 is also provided with a depth-adjusting means 45 whereby the depth at which the cleats are positioned within cavity 48 is adjustable, so as to readily allow the bands to snap over and behind ears 18. That is, the projecting free edges 56 of the head side walls 58 must be positioned with respect to the bracket or tooth, so as to allow the bands to readily snap behind the hooked ears 16, as seen in FIG. 10. The adjusting means 45 comprises a threaded bore 60 adapted to receive a threaded set screw 62, the screw being provided with a butt end 64 which engages the extended cleat members 16 of the bracket. Thus, by adjusting the set screw 62 along bore 60, any particular cleat arrangement of a bracket within cavity 48 is possible.

There is provided an ejector housing 65 which is defined by ejector sleeve 66, the ejector sleeve being slidably mounted over the loading-core member 32, and the core being held in place by means of a spring 67. The spring is formed to fit snugly about rear-guide-stem portion 36 and is positioned within the rear portion of bore 68, the spring being interposed between threaded guide bushing 70 and annular shoulder 71, defining a second spring-retainer means. Stem portion 34 is located in bore 68 forwardly of shoulder 71, the spring retainer 38 having a diameter small enough to pass through the reduced diameter bore 72' of shoulder 71, so as to engage spring 67 when required. The diameter of bore 68 of sleeve 66 is sufficiently large to allow a plurality of elastic bands 26 to be stored therein while being mounted to core 32, as seen in FIG. 7.

The ejector end of housing 65 is formed having a dispenser head 72 which is similar in configuration to the ejector head 44. That is, the dispenser head 72 comprises a pair of oppositely disposed side walls 74, each wall being provided with inwardly tapered notches 75 similar to notches 52, and a countersunk notch or recess 76, the two notches 75 and 76 allowing dispenser head 72 to fit over arch wire 24, so as to guide it into cleat recess 22 when an elastic band is ejected therefrom. Side walls 74 are juxtaposed to side walls 50 of the ejector head; and the upper and lower side walls 78 of the dispenser head 72 are juxtaposed to corresponding walls 58 of ejector head 44. Both heads 44 and 72 have substantially rectangular box-like configurations, whereby ejector head 44 is adapted to be received in dispenser head 72, as seen in FIG. 10.

OPERATION

As previously mentioned, typical orthodontic arch brackets 10 are properly secured to the teeth 14, generally on the outer surface thereof. A conventional metal arch wire 24 is positioned in predetermined relation to the brackets and teeth (seen in FIG. 2), so as to be secured to the brackets in a fixed arrangement by means of the elastic bands 26, as typically shown in FIG. 1.

In order to secure each band 26 to each bracket in the simplest manner, one can now utilize the present invention by employing the following steps.

First, instrument 30 is loaded by removing loading core 32 from housing 65. A plurality of elastic bands 26 are forced over the tapered end 42 of guide-stem portion 36 and over shoulder 38, so as to be supported on intermediate stem portion 34, as seen in FIG. 6. When sufficient numbers of bands are in place, loading core 32 is inserted back into housing 65 through bore 68, so that the tapered guide stem projects from bushing 70 and ejector head 44 is still extended forwardly of ejector head 72, as seen in FIG. 7.

It should be noted that bushing 70 also defines the loading-core-alignment means, which allows ejector head 44 and dispenser head 72 to be fixed in matching alignment with each other during loading and ejecting of the bands. That is, bushing 70 comprises an annular flange 80 and a bore 82, the bore 82 being formed having flat sides 84 so as to receive corresponding flat sides 86 of stem portion 36. Thus, when all of the flat sides are in matching alignment, the ejector head 44 and the dispenser head 72, together with their corresponding notches 52 and 75 and recesses 54 and 76, are also in matching alignment. After core 32 is loaded, sleeve 66 is moved rearwardly to expose the elastic bands 26. The first exposed band is moved forwardly to a position on ejector head 44, as illustrated in FIGS. 7 and 9. Sleeve 66 is then returned to an ejector position (seen in FIG. 4); and at this time ejector head 44 is firmly positioned over the cleats of a slective bracket, as seen in FIG. 9. Sleeve 66 is thus pushed forwardly against tooth 14, allowing head 72 to engage the selected band, force it over ejector head 44, and eject it from head 44, so as to be caught behind hook-ear members 18 of cleat 16, as illustrated in FIG. 10. In addition, arch wire 24 is simultaneously forced into recess 22 formed in cleat 16; and thus the elastic band is not only hooked to cleat 16 but also laps over arch wire 24, securing the wire in its pre-selected position. As the instrument is removed from the bracket-loading core, it will again slide outwardly under the biasing force of spring 67.

It is also important to note that the oppositely disposed walls 78 include a projecting arcuate leading edge 90 (seen in FIG. 11). This arcuate edge prevents any binding of the elastic band between the ejector head 44 and dispenser head 72, as the dispenser head moves forwardly over the ejector head.

The invention and its attendant advantages will be understood from the foregoing description; and it will be apparent that various changes may be made in the form, construction and arrangement of the parts of the invention without departing from the spirit and scope thereof or sacrificing its material advantages, the arrangement hereinbefore described being merely by way of example; and I do not wish to be restricted to the specific form shown or uses mentioned, except as defined in the accompanying claims.

I claim:

1. In combination, an orthodontic instrument for mounting elastic bands about the cleats of brackets affixed to a patient's teeth, whereby an arch wire is selectively secured to the brackets, said combination comprising:

a bracket adapted to be secured to one or more of said patient's teeth, said bracket including extending cleats which are formed to receive the arch wire by means of an elastic band that is positioned around said arch wire and said cleats;

an elongated band-loading core having a rear-guide portion and an intermediate portion arranged to support and store a plurality of said elastic bands which are individually ejected therefrom;

an ejector head formed on one end of said intermediate portion of said loading core, said ejector head having an enlarged cavity formed therein to receive each of said cleats of each of said brackets wholly within said cavity, whereby said band is ejected behind said cleats for positive engagement therewith, said ejector head including a first pair of notches to allow said arch wire to engage therein and be positioned in said cleats;

an elongated ejector housing adapted to be slidably mounted on said band-loading core for longitudinal reciprocal movement thereon;

a dispenser head formed at one end of said housing and including a second pair of notches formed therein, whereby said dispenser head is adapted to be positioned over said ejector head when mounting each of said bands over each of said cleats and said arch wire;

guide means attached to the opposite end of said ejector housing and adapted to receive said rear-guide portion of said loading core, whereby said ejector head and said dispenser head are held in corresponding aligned relationship to each other;

a biasing means disposed in said housing to provide a biasing force between said housing and said band-loading core;

means for securing said loading core in said housing; and an adjusting means to adjust the position of said cleats within said cavity of said ejector head to accommodate various sizes of brackets and their respective cleats, whereby said band is ejected rearwardly of sid cleats.

2. An orthodontic instrument as recited in claim 1, wherein said ejector head includes a pair of side walls in which said first pair of notches are formed; and wherein said dispenser head includes a pair of side walls, each having said second pair of aligned notches formed therein, said notches in said ejector head being aligned with said notches of said dispenser head, all of said notches engaging said arch wire therein, whereby said arch wire is laterally positioned and held in said cleats as said bands are ejected from said ejector head of said dispenser head.

3. An orthodontic instrument as recited in claim 2, wherein said dispenser head further includes a top and a bottom wall, each of said walls being formed having an arcuate leading edge to engage said bands, so as to prevent binding of said bands between said ejector head and said dispenser head.

4. An orthodontic instrument as recited in claim 3, wherein said loading core includes a spring-retainer means, and said housing defines an ejector sleeve having a longitudinal bore and a second spring-retainer means.

5. An orthodontic instrument as recited in claim 3, wherein said guide means comprises a bushing secured to said housing, said bushing having a bore formed having at least one flat side therein, and wherein said guide portion of said loading core is formed having a flat elongated side to engage said flat side of said bore in said bushing, whereby rotation of said loading core in said housing is prevented.

* * * * *